United States Patent
Zia-Ebrahimi

Patent Number: 5,243,053
Date of Patent: Sep. 7, 1993

[54] METHYLENE MELDRUM'S ACID PRECURSORS

[75] Inventor: Mohammad Zia-Ebrahimi, Indianapolis, Ind.

[73] Assignee: Eli Lilly and Company, Indianapolis, Ind.

[21] Appl. No.: 842,844

[22] Filed: Feb. 26, 1992

[51] Int. Cl.$^5$ .......................... C07D 405/06
[52] U.S. Cl. .................. 546/268; 546/207; 544/109
[58] Field of Search ............ 549/274; 546/207, 268; 544/109

[56] References Cited

U.S. PATENT DOCUMENTS 4,613,671  9/1986  Relenyi et al. ............. 549/274

OTHER PUBLICATIONS

Margaretha et al., Monatshefte für Chemie, vol. 100, pp. 576–583 (1969).
Chemical Abstracts, vol. 71, No. 4, Abstract 22084y, p. 327, Jul. 28, 1969.
Meldrum, *J. Chem. Soc.*, 93, 598 (1908).
Davidson, et al., *J. Am. Chem. Soc.*, 70, 3426 (1948).
Corey, *J. Am. Chem. Soc.*, 74, 5897 (1952).
Snyder, et al., *J. Am. Chem. Soc.*, 80, 1942 (1958).
Hedge, et al., *J. Org. Chem.*, 26, 3166 (1961).
McNab, *Chem. Soc. Rev.*, 7, 345 (1978).
Brown, et al., *Aust. J. Chem.*, 30, 179 (1977).
Mitscher, et al., *Tetrahedron Letters*, 24(44), 4809 (1983).
Buzinkai, et al., *Tetrahedron Letters*, 26(27), 3195 (1985).
Jung, et al., *Tetrahedron Letters*, 27(51), 6165 (1986).
Jung, et al., *J. Am. Chem. Soc.*, 110, 3965 (1988).
Dissertation of Keith R. Buszek, University of California, Los Angeles, 1987.
Kunz, et al., *Monatsh. Chem.*, 100, 920 (1969).

*Primary Examiner*—Bernard Dentz
*Attorney, Agent, or Firm*—Robert A. Conrad; Leroy Whitaker

[57] ABSTRACT

This invention provides new stabilized methylene Meldrum's acid precursors, a process for their preparation, and a process for using such compounds in the preparation of methylene Meldrum's acid.

20 Claims, No Drawings

METHYLENE MELDRUM'S ACID PRECURSORS

BACKGROUND OF THE INVENTION

The unusually low pKa of the methylene protons of Meldrum's acid (2,2-dimethyl-1,3-dioxane-4,6-dione; A. N. Meldrum, *J. Chem. Soc.*, 93, 598 (1908)) and the ability of its ester groups to undergo hydrolysis under very mild conditions make it an excellent alternative for malonic acid in reactions in which vigorous conditions are to be avoided. Reactions of this species with carbonyl compounds and some alkyl halides have been reported (D. Davidson and S. A. Bernhard, *J. Am. Chem. Soc.*, 70, 3426 (1948); E. J. Corey, *J. Am. Chem. Soc.*, 74, 5897 (1952); H. R. Snyder and C. W. Kruse, *J. Am. Chem. Soc.*, 80, 1942 (1958); J. W. Hedge, C. W. Kruse, and H. R. Snyder, *J. Org. Chem.*, 26, 3166 (1961)).

Methylene Meldrum's acid (II) has been reported as a compound with high reactivity as a dienophile, as well as a Michael acceptor. (H. McNab, *Chem. Soc. Rev.*, 7, 345 (1978); F. J. Kunz and O. E. Polansky, *Monatsh. Chem.*, 100, 920 (1969); R. F. C. Brown, F. W. Eastwood, and G. L. McMullen, *Aust. J. Chem.*, 30, 179 (1977)). This species, however, can only be generated in situ as an intermediate and cannot be isolated. In Diels-Alder reactions, for instance, it is generated in a one-pot reaction by adding a 37% aqueous solution of formaldehyde to a solution containing the diene and Meldrum's acid. Diisopropylidene methylenedimalonate (III), the aldol-Michael bis adduct of Meldrum's acid and formaldehyde, has been shown to be a source of methylene Meldrum's acid for the addition of substituted three-carbon units to monohydroxyanthraquinones in Michael-type reactions (Mitscher, et al., *Tetrahedron Letters*, 26, 3195 (1985)).

It has also been shown that III and one equivalent of formaldehyde improve the yields of Diels-Alder reactions when used instead of Meldrum's acid and formaldehyde. The mechanism by which this reaction proceeds presumably involves the addition of formaldehyde to one of the two Meldrum's acids at the 5-position, followed by cleavage of the C—C bond and elimination of water to give two methylene Meldrum's units as shown in the following "speculative" mechanism suggested by J. F. Buzinkai, et al., *Tetrahedron Letters*, 26, 3195 (1985):

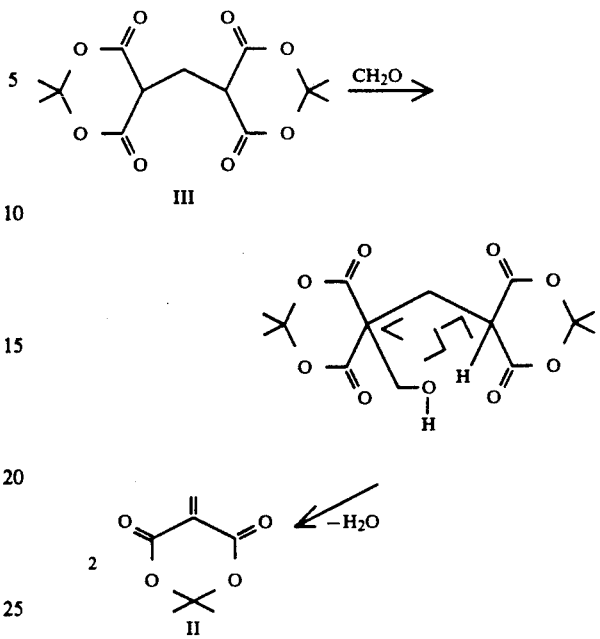

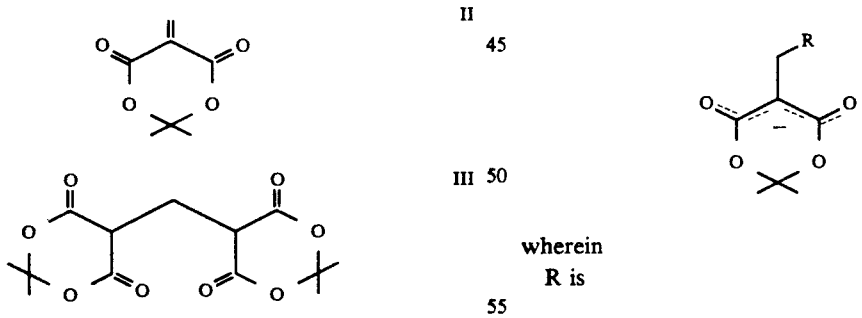

For all intents and purposes, III is a protected form of methylene Meldrum's acid which enhances the yields of Diels-Alder reactions, but not without side products. III has not proved to be very effective in Michael reactions.

This invention provides compounds which are new stabilized precursors of methylene Meldrum's acid which greatly enhance the yields of reactions which would normally involve methylene Meldrum's acid.

SUMMARY OF THE INVENTION

This invention provides new stabilized methylene Meldrum's acid precursors of the Formula I wherein
R is

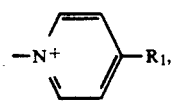

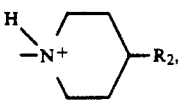

or

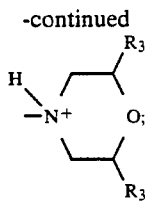

$R_1$ is hydrogen, $C_1$-$C_4$ alkyl, halo, or dimethylamino;
$R_2$ is hydrogen or methyl; and
each $R_3$ is independently hydrogen or methyl.

Also provided is a process for preparing methylene Meldrum's acid II which comprises contacting a compound of Formula I as described above with an acid. In addition, this invention provides a process for preparing compounds of Formula I.

DETAILED DESCRIPTION AND PREFERRED EMBODIMENT

The following definitions refer to the various terms used throughout this disclosure. "$C_1$-$C_4$ alkyl" refers to straight and branched aliphatic radicals of one to four carbon atoms such as methyl, ethyl, propyl, isopropyl, n-butyl, sec-butyl, and tert-butyl. The term "halo" refers to fluoro, chloro, bromo, and iodo.

The preferred compounds of this invention are those compounds of Formula I wherein $R_1$, $R_2$, or $R_3$, as appropriate, are hydrogen. Particularly preferred is the pyridinium compound 1-[(6-hydroxy-2,2-dimethyl-4-oxo-4H-1,3-dioxin-5-yl)methyl]pyridinium hydroxide, inner salt (Ia).

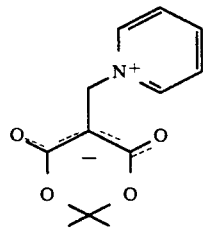

The synthesis of I is accomplished by a simple and high-yielding reaction (>90%) involving the addition of one equivalent of formaldehyde, usually supplied as a 37% by weight solution of formaldehyde in water, to Meldrum's acid in presence of the appropriate pyridine, piperidine, or morpholine base. Although I, over time, spontaneously converts into methylene Meldrum's acid (II), the addition of an acid, such as acetic acid or a mineral acid, preferably hydrochloric acid, to a solution of I, preferably in a non-reactive solvent such as chloroform, dichloromethane, an alcohol, or the like, facilitates the conversion of II to I usually in essentially quantitative yield. Thus, contacting I with an acid provides a facile process of generating II which is used In situ for subsequent reaction. This sequence is summarized in the scheme below using Ia for illustration purposes:

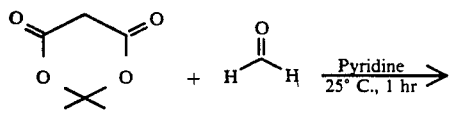

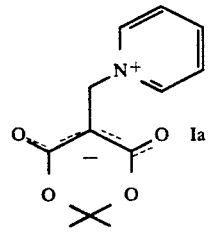

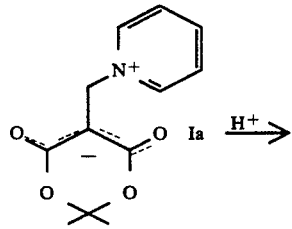

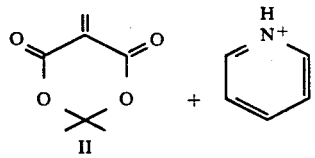

In the preparation of I, it is preferred that approximately equimolar amounts of Meldrum's acid and formaldehyde are employed; although other ratios are operative, the results will be dependent upon the limiting reagent. Similarly, it is preferred that at least one molar equivalent of the pyridine, piperidine, or morpholine base be employed; again, other ratios are operative but results will be dependent upon the limiting reagent. When no more than a molar equivalent of base is employed, it is preferred that the reaction be facilitated by the presence of a non-reactive solvent, such as an alcohol. For example, upon mixing equimolar amounts of Meldrum's acid, formaldehyde, and pyridine in ethanol, after a few minutes the reaction mixture produces a white precipitate which is found to be III. When the mixture is allowed to stir for an additional 16 hours, the solution turns yellow and homogeneous again. Reducing the solution in vacuo produces a yellow crystalline material which was determined to be Ia. Thus, using one equivalent of base, the reaction proceeds to completion in about 10–20 hours. Alternatively, a (molar) excess of base can be employed to serve both as reagent and solvent. As above, reacting Meldrum's acid with formaldehyde and one equivalent of pyridine in ethanol produces white crystalline III. Adding a second equivalent of pyridine to the reaction mixture will give the desired product, Ia, within a few minutes. Excess pyridine can easily be removed in vacuo.

Alkenylpyridinium and alkenyltrialkylammonium compounds have previously been used in Diels-Alder reactions. Buszek and Jung reported that dienophiles anchored to either alkylammonium or pyridinium moieties would undergo Diels-Alder reactions inducing endo additions with excellent yields. (Jung, M. E. and Buszek K. R., *Tet. Lett.*, 51, 6165 (1986); Jung, M. E. and Buszek K. R., *J. Am. Chem. Soc.*, 110, 3965 (1988); Buszek, K. R., Ph.D. Dissertation, University of California, Berkley (1987)). However, these pyridinium or alkylammonium compounds are typically tetrafluoroborate salts or halides, as opposed to inner salts or betaines as presented in this invention. Also, in the former compounds pyridine itself is part of the Diels-Alder adduct whereas in the present invention the pyridine (i.e., when employing Ia) is merely a stabilizer for the dienophile.

The use of stabilized precursors I, instead of Meldrum's acid and formaldehyde or III and formaldehyde, greatly enhances the yields of reactions which involve methylene Meldrum's acid. Michael reactions performed with Ia have produced products of very high purity in excess of 70% yields. The same reactions performed with Meldrum's acid and formaldehyde or III and formaldehyde yielded less than 25%. Diels-Alder reactions performed between Ia and cyclohexadiene and 1,3-dimethylbutadiene have produced pure Diels-Alder adducts in essentially quantitative yields (97% or greater), whereas with the use of III and formaldehyde yields in the range of 80–85% are observed. Compound Ia was also used in Michael reactions in the synthesis of VI and VII. Reaction between Ia and ethyl nitroacetate produces analytically pure VI with a 75% yield. Compounds I can be used to synthesize glutamic acid derivatives. Compounds I can also be reacted with indoles to produce VII and derivatives thereof as important intermediates in the synthesis of ergoline partial structures. See, e.g., Flaugh, et al., *J. Med. Chem.*, 31, 1746 (1988); Farlow, et al., *Org. Prep. Proc. Int.*, 13, 39 (1981).

The illustrative compounds synthesized by the method of this invention are shown in the figure below.

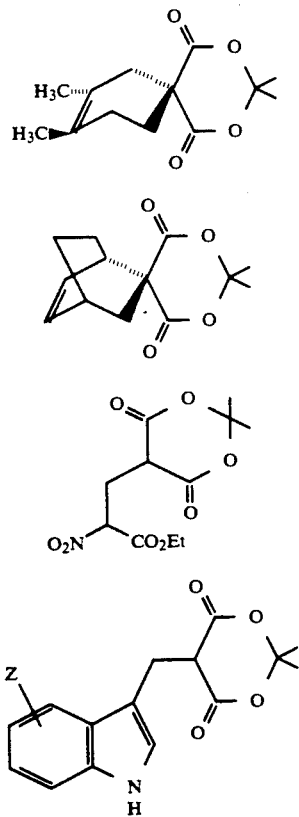

The following examples further illustrate the preparation of compounds I and uses thereof. These examples are illustrative only and are not intended to limit the scope of the invention in any way. Melting points are uncorrected. NMR spectra were run in CDCl₃, unless otherwise specified, on a General Electric QE-300 MHz unit. Mass Spectra are FD's and done on Varian Mat-731 mass spectrometers. Infrared spectra are run on a Nicolet DX 10 Spectrometer. All reagents were used as received from the supplier.

EXAMPLE 1

1-[(6-hydroxy-2,2-dimethyl-4-oxo-4H-1,3-dioxin-5-yl)methyl]pyridinium hydroxide, inner salt (Ia)

Meldrum's acid (20 g, 0.139 mol) was dissolved in 50 ml of pyridine. The solution immediately turned yellow and was somewhat exothermic. After dissolution was complete, a 37% aqueous solution of formaldehyde (10.4 ml, 0.139 mol) was added in one portion. The reaction mixture was allowed to stir for one hour under argon. The solvent was removed in vacuo at 55° C. after which yellow crystals were isolated. These crystals were then stirred with 200 ml of hexanes for 30 minutes and filtered providing 32.24 g (0.127 mol, 91.6%) of the desired title product. Melting point: >350° C. NMR (ppm): 1.62 (s, 6H (CH₃)); 5.58 (bs, 2H (CH₂)); 7.71 (t, 2H (Ar-H)); 8.17 (t, 1H (Ar-H)); 9.0 (d, 2H (Ar-H)). MS: 235.23.

EXAMPLE 2

Methylene Meldrum's acid (II)

A solution of 5 mg of Ia in 0.5 ml of CDCl₃ in an NMR tube under an argon atmosphere was shaken with one equivalent of a 20% solution of DCl. Small crystals formed in the tube. NMR (ppm): 1.73 (s, 6H (CH₃)); 7.16 (s, 2H, (vinyl H)). MS: 156.

EXAMPLE 3

3,3,8,9-Tetramethyl-2,4-dioxospiro[5.5]undec-8-ene-1,5-dione (IV)

A solution of 0.50 g of Ia (1.97 mmol) in 15 ml of absolute ethanol was added through an addition funnel over a period of five minutes to a stirred solution of 0.22 ml (1.97 mmol) of 2,3-dimethyl-1,3-butadiene. The reaction mixture was stirred at room temperature for one hour. The mixture was then poured over 50 ml ice water upon which the product crystallized. Compound IV was obtained as white crystals (0.47 g, 99.7%) by filtration. Melting point: 90.6°–91.0° C. NMR (ppm): 1.65 and 1.68 (2 s, 6H, (gem methyl groups)); 1.71 (s, 3H, (CH₃)); 1.75 (s, 3H, (CH₃)); 2.12 (s, 4H, (CH₂)) ; 2.49 (s, 2H, (CH₂)). MS: 238.

EXAMPLE 4

2′,2′-Dimethyl 4′,6′-dioxospiro[bicyclo[2.2.2]-5-octene]-2,5′-[1,3]dioxane (V)

A solution of 0.50 g of Ia (1.97 mmol) in 10 ml absolute ethanol was added slowly through an addition funnel to a stirred solution of 0.19 ml (1.97 mmol) of cyclohexadiene. The reaction mixture was stirred for one hour at 25° C., then reduced vacuo and taken up in 50 ml of diethyl ether. After washing with three 50 ml portions of cold water, the organic phase was separated, dried over magnesium sulfate, filtered and reduced in vacuo to give a crystalline material which upon recrystallization from ethanol yielded 0.43 g (92.4%) of the desired product V. Melting point: 78.7°–79.1° C. NMR (ppm): 1.18–1.25 (m, 4H (two H7 and two H8)); 1.65 and 1.80 (2 s, 3H (gem methyl)); 2.01 (m, 1H (H3 endo));

2.23 (m, 1H (H3 exo)); 2 81 (br s, 1H (H4)); 2.97 and 2.99 (br. d, 1H (H1)); 6.10 (t, 1H (H5)); 6.45 (t, 1H (H6)). MS: 236.

EXAMPLE 5

(+,−)-2,3-Dimethyl-α-nitro-4,6-dioxo-1,3-dioxane-5-propionic acid ethyl ester (VI)

A solution of Ia (9.21 g, 36.4 mmol) in 35 ml of absolute ethanol was added to a stirred solution of ethyl nitroacetate (4.00 ml, 36.4 mmol) and 2.10 ml of glacial acetic acid in 20 ml of absolute ethanol slowly over a period of 10 minutes at room temperature. The solution was stirred an additional 15 minutes after which it was reduced in vacuo. The residue was dissolved in 50 ml of chloroform and washed with 1N hydrochloric acid (3×50 ml). The organic phase was concentrated under reduced pressure to provide a light yellow oil. Twenty milliliters of diethyl ether were added and the flask was chilled under a stream of nitrogen after which 30 ml of hexanes were added slowly while stirring. Compound VI was isolated in 74.9% yield (7.88 g) by filtering the resulting white crystals. Melting point: 77.0°–77.3° C. NMR (ppm): 1.31 (t, 3H (ethyl $CH_3$)); 1.8 (d, 6H (gem dimethyl)); 2.88–2.98 (m, 2H (methylene)); 3.87 (t, 1H (methine, γ to $NO_2$)); 4.33 (q, 2H (ethyl $CH_2$)), 5.76 (s, 1H (methine, α to $NO_2$)). MS: 289.24.

EXAMPLE 6

5-(Indole-3-methyl)-2,2-dimethyl-1,3-dioxane 4,6-dione (VII)

A solution of Ia (0.50 g, 2.13 mmol) in absolute ethanol was added slowly to a stirring solution of indole (0.25 g, 2.13 mmol) and 0.12 ml of glacial acetic acid in ethanol. This solution was stirred for one hour, after which it was evaporated n vacuo. The residue was dissolved in 20 ml of hot methanol. To this was added 25 ml of cold water in one portion. The tan crystals that resulted were recrystallized from methanol to give 0.48 g (82.5%) of pure VII, melting point: 109.5°–110° C. (lit. 106°–108° C.). NMR (ppm): 1.45/1.70 (2 s, 6H, gem dimethyl); 3.65 (d, 2H, methylene); 3.75–3.78 (t, 1H, methine); 7.11–7.34 (m, 4H aromatic); 7.70–7.73 (d, 1H, N-CH=C); 8.03 (broad s, 1H, N). MS: 273.

Alternate procedure for preparing I

Meldrum's acid is added to 10.20 ml ethanol (does not completely dissolve), followed by the addition of 1 equivalent of base, and 1 equivalent of 37% aqueous formaldehyde solution. The reaction mixture is stirred at room temperature for 16 hours. The reaction is then concentrated in vacuo and triturated with 50/50 hexane/diethyl ether to give the desired product I. Results from this procedure for representative compounds are summarized in the following table:

| Base | Product Structure | yeild | melting point (°C.) |
|---|---|---|---|
| 4-iodopyridine | Ie | 92.5% | 146.8 |
| pyridine | Ia | 94.9% | >350 |
| morpholine | Id | 72.0% | 149.8 |
| 4-dimethylaminopyridine | Ib | 91.4% | sublimes |
| piperidine | Ic | 72.3% | 159.6 |

-continued

| Base | Product Structure | yeild | melting point (°C.) |
|---|---|---|---|
| | Ib | | |
| | Ic | | |
| | Id | | |
| | Ie | | |

I claim:
1. A compound of the formula

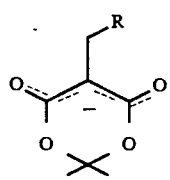

wherein R is

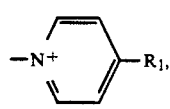

-continued

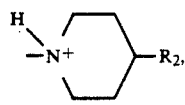

or

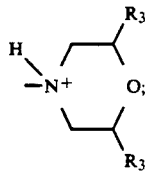

$R_1$ is hydrogen, $C_1$-$C_4$ alkyl, halo, or dimethylamino; $R_2$ is hydrogen or methyl; and each $R_3$ is independently hydrogen or methyl.

2. A compound of claim 1 wherein R is

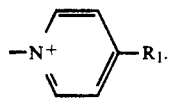

3. A compound of claim 1 wherein R is

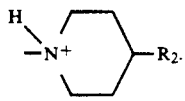

4. A compound of claim 1 wherein R is

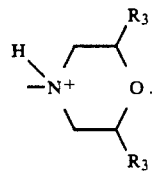

5. The compound of claim 2 which is 1-[(6-hydroxy-2,2-dimethyl-4-oxo-4H-1,3-dioxin-5-yl)methyl]-pyridinium hydroxide, inner salt.

6. A process for preparing a compound of the formula

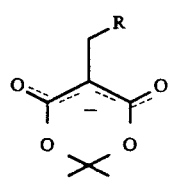 I wherein
R is

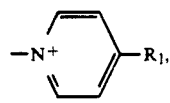

-continued

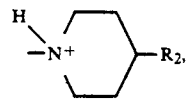

or

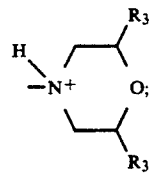

$R_1$ is hydrogen, $C_1$-$C_4$ alkyl, halo, or dimethylamino; $R_2$ is hydrogen or methyl; and each $R_3$ is independently hydrogen or methyl; which comprises combining Meldrum's acid, formaldehyde, and a base selected from the group consisting of

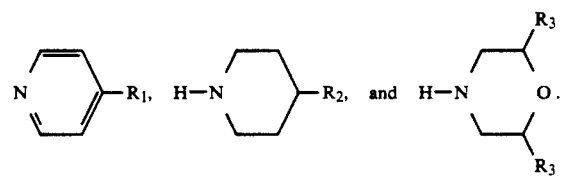

7. The process of claim 6 wherein the formaldehyde is present as 37% formaldehyde in water.

8. The process of claim 6 wherein approximately equimolar amounts of the Meldrum's acid and formaldehyde are employed.

9. The process of claim 8 where approximately an equimolar amount of base employed.

10. The process of claim 9 wherein a non-reactive solvent is also employed.

11. The process of claim 10 wherein the solvent is an alcohol.

12. The process of claim 1 wherein the solvent is ethanol.

13. The process of claim 8 wherein a molar excess of base is employed.

14. The process of claim 6 wherein the base is pyridine.

15. The process of claim 13 wherein the base is pyridine.

16. A process for preparing methylene Meldrum's acid which comprises contacting a compound of the Formula

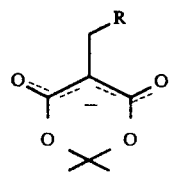 I wherein
R is

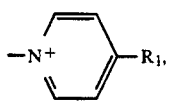

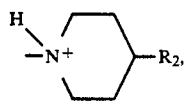

or

-continued

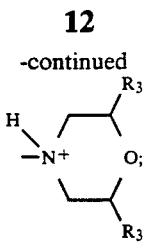

$R_1$ is hydrogen, $C_1$–$C_4$ alkyl, halo, or dimethylamino; $R_2$ is hydrogen or methyl; and each $R_3$ is independently hydrogen or methyl; with an acid.

17. The process of claim 16 wherein the acid is a mineral acid.

18. The process of claim 17 wherein the acid is hydrochloric acid or acetic acid.

19. The process of claim 16 wherein the acid and compound are contacted in the presence of a non-reactive solvent.

20. The process of claim 16 wherein the compound is 1-[(6-hydroxy-2,2-dimethyl-4-oxo-4H-1,3-dioxin-5-yl)methyl]pyridinium hydroxide, inner salt.

* * * * *

UNITED STATES PATENT AND TRADEMARK OFFICE
CERTIFICATE OF CORRECTION

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 2, lines 10-20 the formula reading

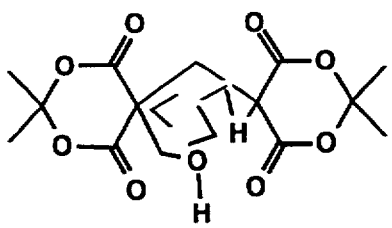

should read

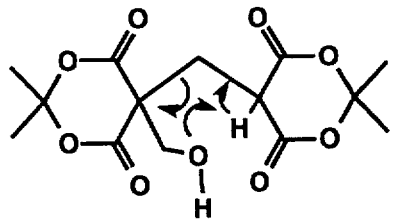

UNITED STATES PATENT AND TRADEMARK OFFICE
CERTIFICATE OF CORRECTION

PATENT NO.    :   5,243,053

DATED         :   Sept. 7, 1993

INVENTOR(S)   :   Mohammad Zia-Ebrahimi

It is certified that an error appears in the above-identified patent and that said Letters Patent is hereby corrected as shown below:

Column 3, lines 2-8 the formula reading

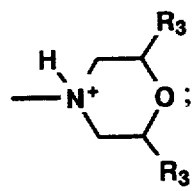

should read

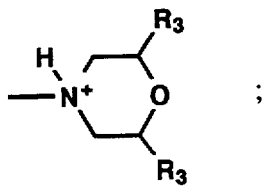

UNITED STATES PATENT AND TRADEMARK OFFICE
CERTIFICATE OF CORRECTION

PATENT NO. : 5,243,053

DATED : Sept. 7, 1993

INVENTOR : Mohammad Zia-Ebrahimi

It is certified that an error appears in the above-identified patent and that said Letters Patent is hereby corrected as shown below:

Column 6, line 12, "50 ml of pyridine" should read --150 ml of pyridine--.

Column 6, line 64, "vacuo to give a crystalline material" should read --vacuo to give a white crystalline material--.

UNITED STATES PATENT AND TRADEMARK OFFICE
CERTIFICATE OF CORRECTION

PATENT NO. : 5,243,053
DATED : Sept. 7, 1993
INVENTOR(S) : Mohannad Zia-Ebrahmimi It is certified that error appears in the above-indentified patent and that said Letters Patent is hereby corrected as shown below:

Column 8, lines 5-15 the formula reading

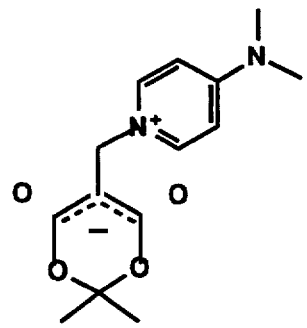

Ib should read

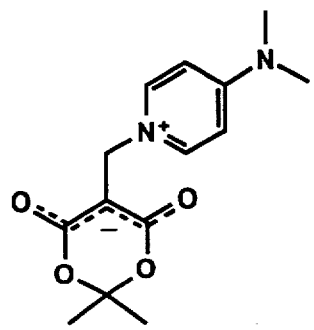

Ib

UNITED STATES PATENT AND TRADEMARK OFFICE
CERTIFICATE OF CORRECTION

Page 5 of 12

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 8, lines 17-27 the formula reading

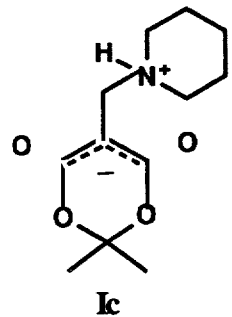

should read

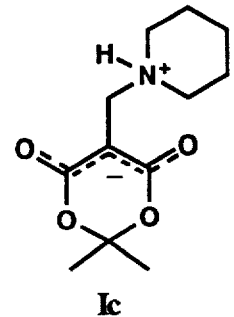

UNITED STATES PATENT AND TRADEMARK OFFICE
CERTIFICATE OF CORRECTION

PATENT NO.   :   5,243,053

DATED        :   Sept. 7, 1993

INVENTOR(S)  :   Mohammad Zia-Ebrahimi

It is certified that an error appears in the above-identified patent and that said Letters Patent is hereby corrected as shown below:

Column 8, lines 28-39 the formula reading

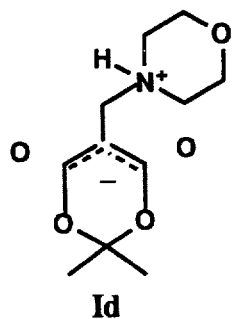

Id should read

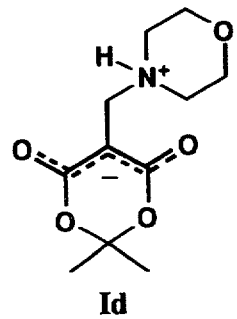

Id

UNITED STATES PATENT AND TRADEMARK OFFICE
CERTIFICATE OF CORRECTION

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 8, lines 40-49 the formula reading

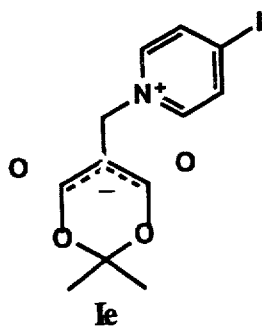

should read

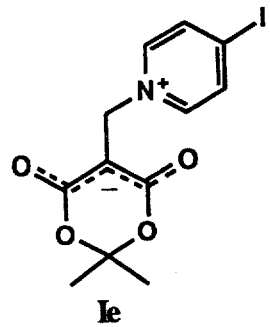

UNITED STATES PATENT AND TRADEMARK OFFICE
CERTIFICATE OF CORRECTION

PATENT NO.   :   5,243,053

DATED        :   Sept. 7, 1993

INVENTOR(S)  :   Mohammad Zia-Ebrahimi

It is certified that an error appears in the above-identified patent and that said Letters Patent is hereby corrected as shown below:

Column 9, lines 10-16 the formula reading

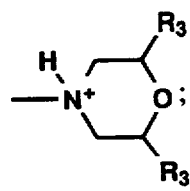

should read

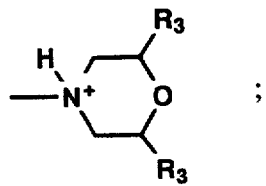

UNITED STATES PATENT AND TRADEMARK OFFICE
CERTIFICATE OF CORRECTION

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 9, lines 37-45 the formula reading

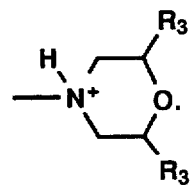

should read

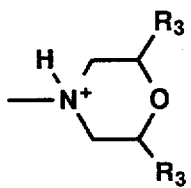

UNITED STATES PATENT AND TRADEMARK OFFICE
CERTIFICATE OF CORRECTION

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 10, lines 10-16 the formula reading

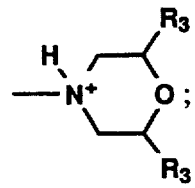

should read

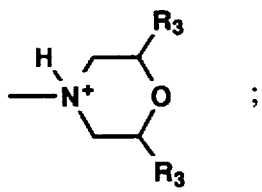

UNITED STATES PATENT AND TRADEMARK OFFICE
CERTIFICATE OF CORRECTION

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 10, lines 25-32 the formula reading

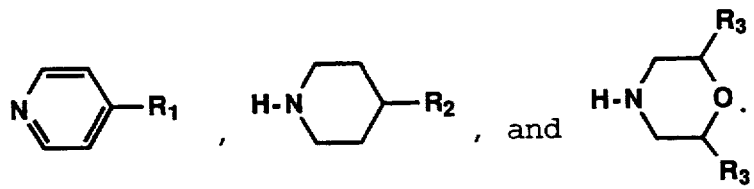

should read

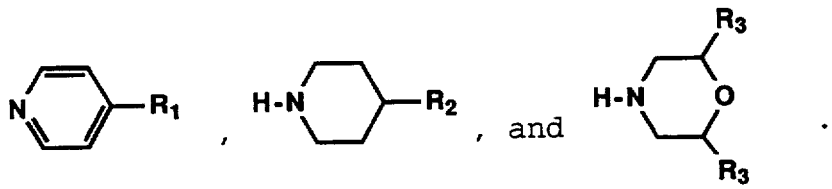

UNITED STATES PATENT AND TRADEMARK OFFICE
CERTIFICATE OF CORRECTION

PATENT NO. : 5,243,053

DATED : Sept. 7, 1993

INVENTOR(S) : Mohammad Zia-Ebrahimi

It is certified that an error appears in the above-identified patent and that said Letters Patent is hereby corrected as shown below:

Column 12, lines 2-8 the formula reading

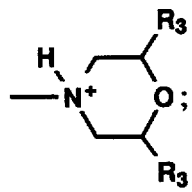

should read

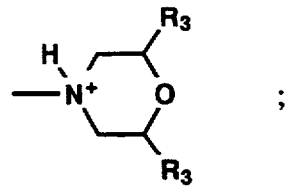

Signed and Sealed this

Twenty-second Day of November, 1994

Attest:

BRUCE LEHMAN

Attesting Officer

Commissioner of Patents and Trademarks